United States Patent [19]
Tamura et al.

[11] Patent Number: 5,637,322
[45] Date of Patent: Jun. 10, 1997

[54] METHOD FOR PRODUCING COMPOSITION FOR SOLID MEDICINE

[75] Inventors: Kiyoshi Tamura; Ken-ichi Sugimori, both of Takatsuki; Kenji Ogawa, Chikujo-gun, all of Japan

[73] Assignees: Japan Tobacco Inc., Tokyo; Yoshitomi Pharmaceutical Industries Ltd., Osaka, both of Japan

[21] Appl. No.: 433,351

[22] PCT Filed: Nov. 5, 1993

[86] PCT No.: PCT/JP93/01603

§ 371 Date: Jun. 15, 1995

§ 102(e) Date: Jun. 15, 1995

[87] PCT Pub. No.: WO94/10998

PCT Pub. Date: May 26, 1994

[30] Foreign Application Priority Data

Nov. 6, 1992 [JP] Japan .................................. 4-321427

[51] Int. Cl.$^6$ ................................ A61K 9/20; A61K 9/22
[52] U.S. Cl. ................................ 424/494; 424/495
[58] Field of Search ........................ 424/78.08, 494, 424/495

[56] References Cited

U.S. PATENT DOCUMENTS

| | | | |
|---|---|---|---|
| 4,656,027 | 4/1987 | Sjoovist | 424/495 |
| 4,720,387 | 1/1988 | Sakamoto et al. | 424/472 |
| 4,822,808 | 4/1989 | Lida et al. | 514/355 |
| 5,011,837 | 4/1991 | Atwal et al. | 514/227.8 |
| 5,250,547 | 10/1993 | Lochead et al. | 514/337 |
| 5,447,943 | 9/1995 | Lochead et al. | 514/337 |

*Primary Examiner*—Shelley A. Dodson
*Attorney, Agent, or Firm*—Wenderoth, Lind & Ponack

[57] ABSTRACT

In producing a composition for solid medicine, comprising, as an active ingredient, a potassium channel activator and a pharmaceutically acceptable water-insoluble cellulose polymer, a method for producing a composition for solid medicine, which is characterized by dissolving a potassium channel activator in a solvent to give a medical solution, adding said medical solution to a water-insoluble cellulose polymer inert to said solvent in an amount necessary and sufficient to achieve a predetermined elution rate, homogeneously mixing them and drying the mixture to remove the solvent, and a composition for solid medicine, which is obtainable by said production method. According to the method of the present invention, elution rate of the active ingredient of a preparation comprising a potassium channel activator, which is a sustained release preparation, can be controlled with ease and with good reproducibility.

10 Claims, 3 Drawing Sheets

○———○ Example 1
■- - - -■ Example 2
●-·-·-● Example 3
▲·········▲ Example 4

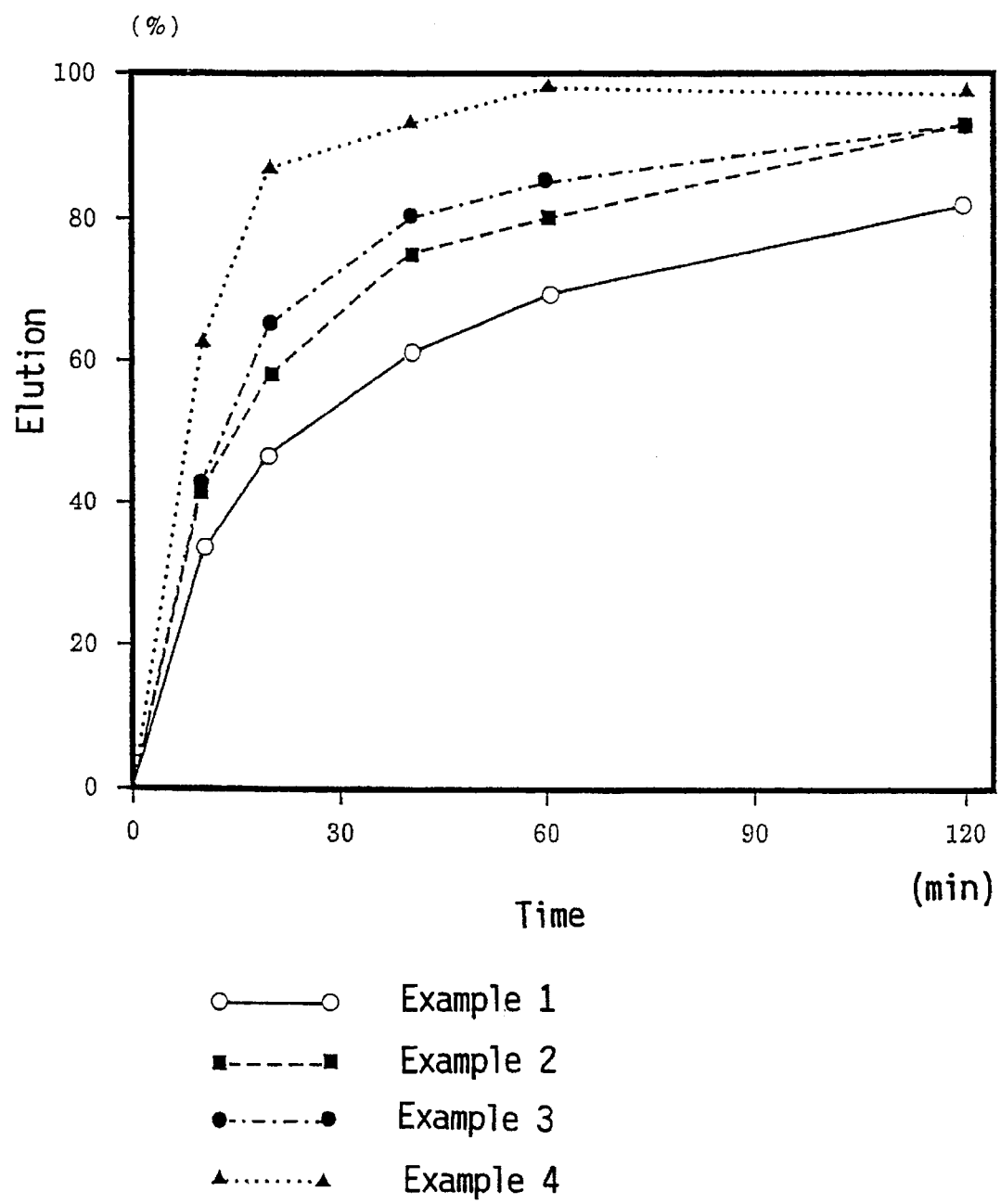

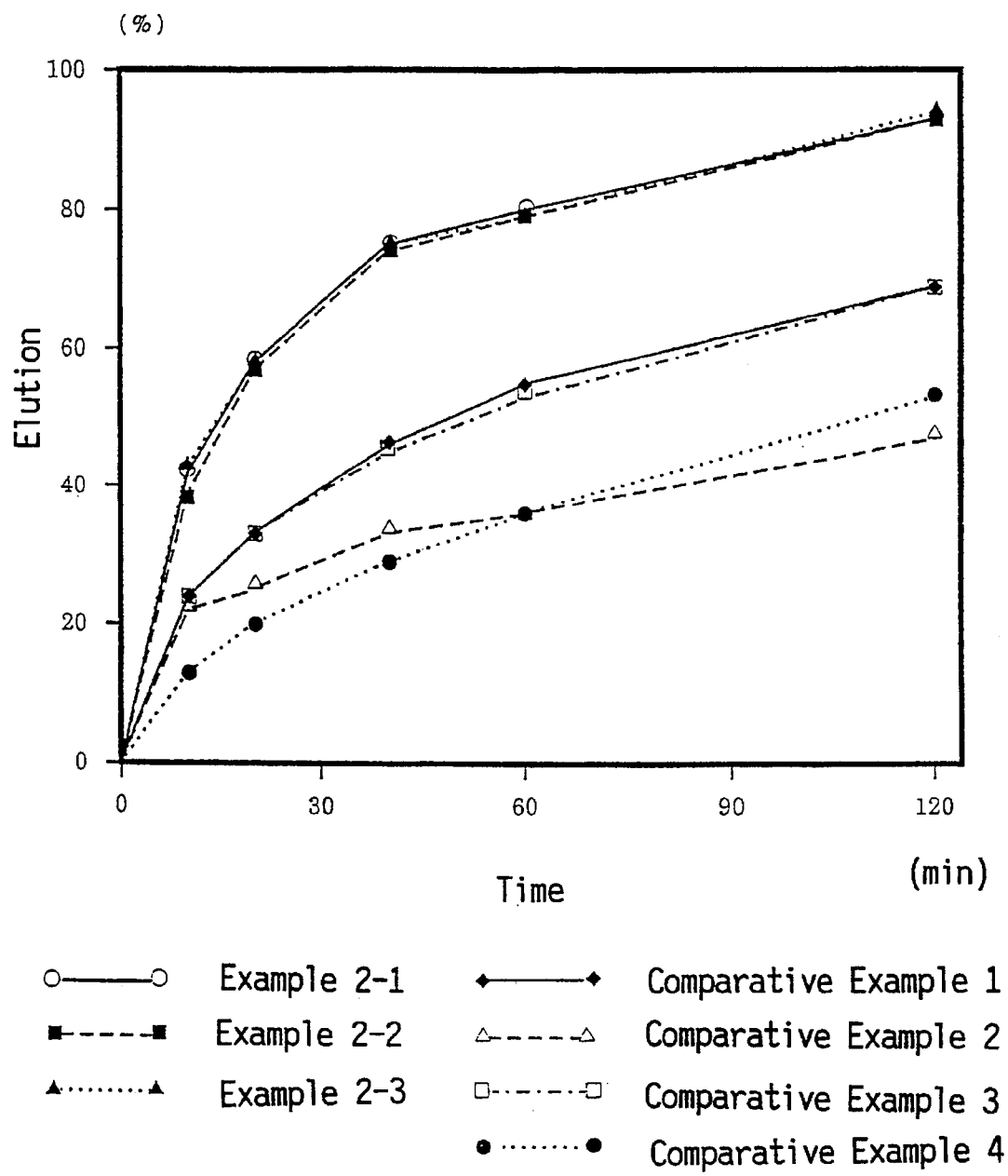

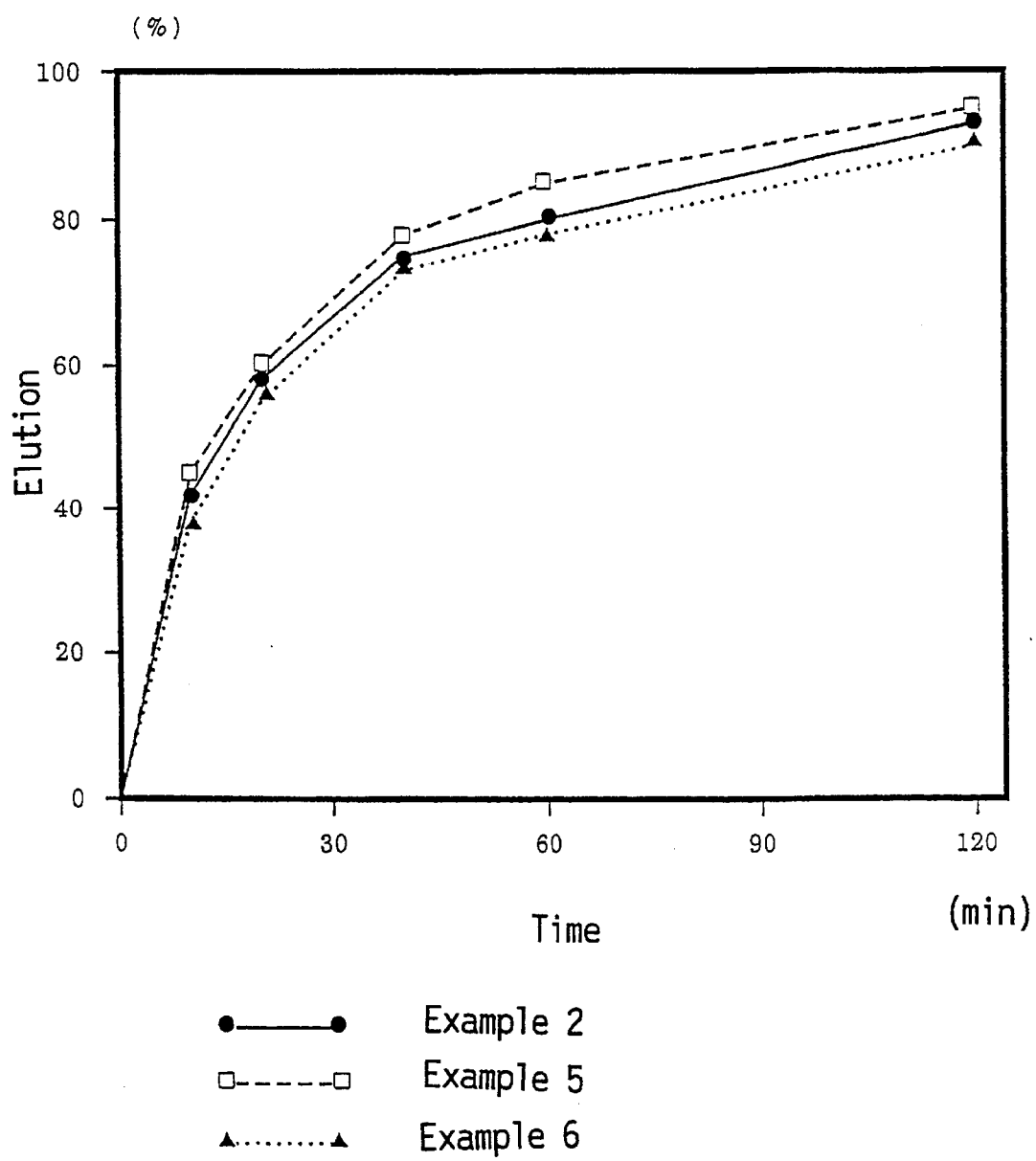

1

METHOD FOR PRODUCING COMPOSITION FOR SOLID MEDICINE

BACKGROUND OF THE INVENTION

1. Field of the Invention

The present invention relates to a method for producing a composition for solid medicine, comprising, as an active ingredient, a potassium channel activator (potassium channel opener) useful as an antihypertensive agent and so on. More particularly, the present invention facilitates the control of elution of a potassium channel activator, by formulating same into solid preparations by dissolving a potassium channel activator in a solvent to give a medical solution, homogeneously mixing said solution with a water-insoluble cellulose or cellulose derivatives and removing the solvent by drying.

2. Description of Related Art

A potassium channel activator is an active substance which acts on a potassium channel of cell membranes, and is expected to be effective as an antihypertensive drug and a therapeutic drug for angina pectoris. Typical compounds having such activity are pyridine derivatives such as nicorandil and pinacidil, and chromane derivatives represented by chromakalim, and chromane derivatives have been particularly intensively studied.

The above-mentioned potassium preparations generally show high effects as an antihypertensive agent or coronary vasodilating agent in an extremely small dose. Hence, too rapid a dissolution thereof results in problematic side-effects such as sudden hypotension. Too slow a dissolution thereof, however, makes it difficult to attain sufficient efficacy. In other words, control and adjustment of elution rate are extremely critical for the drug of this kind.

Incidentally, potassium channel activators such as the above-mentioned chromane derivatives and pyridine derivatives are mostly solid chemical substances. When using such solid chemical substance as an active ingredient, said compound is generally produced with great care. However, the compound is not free from variation in the shape and particle size of crystals, and every lot tends to have a different elution rate. A method for controlling the elution rate of these solid drugs has been, for example, a method comprising pulverizing drug crystals to afford uniform particle size of the crystals or a method comprising controlling the elution rate by coating the drug with a mixture of water-soluble and water-insoluble polymers. Yet, pulverizing crystals in a certain range with good reproducibility is not easy, and control of elution rate relying on pulverizing is associated with difficulty. The method comprising coating of the drug is also defective in that the production steps become complicated and the cost tends to be higher.

The excipients for solid preparations such as powder, granule and tablet include, for example, organic excipients such as saccharides (e.g. lactose, glucose, mannit and sorbit), starches (e.g. corn starch and dextrin), celluloses [e.g. crystalline cellulose (MCC), low substituted hydroxypropyl cellulose (L-HPC) and internally crosslinked sodium carboxymethyl cellulose (CMC-Na)], gum arabic, dextran and pullulan; and inorganic excipients such as light anhydrous silicate, synthetic aluminum silicate, calcium phosphate, sodium carbonate and calcium sulfate. Of these, crystalline cellulose permits direct compression and is applied to a wide range of use such as capsule filling auxiliary, granulating auxiliary for granules and spherical granules, oil-absorber and the like, besides the use for compression. As a preparation method using cellulose, the technique such as the following is known.

That is, Japanese Patent Unexamined Publication No. 38322/1985 describes a method for obtaining easily-soluble solid preparation, comprising dissolving a dihydropyridine A, which is useful as an antihypertensive agent or coronary vasodilating agent, in an organic solvent such as chloroform, adding hydroxypropylmethyl cellulose, which is a water-soluble polymer, to this solution to give a homogeneous solution, and removing the organic solvent. The easy dissolution of the drug is ensured by the use of a water-soluble cellulose derivative, unlike control of elution rate by the use of a water-insoluble polymer.

Japanese Patent Unexamined Publication No. 47615/1980 describes a Niphedipine solid preparation containing crystalline cellulose as an excipient, which is stable to light, temperature and humidity, and the production method thereof includes dissolving 10 g of Niphedipine in 500 ml of acetone, allowing same to adsorb on crystalline cellulose, drying, and formulating same into a solid preparation by a conventional method.

However, these literatures do not disclose potassium channel activators, and the addition of a cellulose polymer in an amount necessary and sufficient to achieve a predetermined elution rate and the control of elution rate.

It is therefore an object of the present invention to provide a method for producing a composition for solid medicine, comprising, as an active ingredient, a potassium channel activator, which method permitting easy control of the elution rate of the active ingredient with good reproducibility.

SUMMARY OF THE INVENTION

The present inventors have conducted intensive studies to resolve the above-mentioned defects in the conventional techniques, and found that a composition for solid medicine, which is capable of eliminating variation in elution rate per produced lot and controlling initial elution rate, can be prepared with good reproducibility by markedly simple steps of dissolving a potassium channel activator as an active ingredient in a solvent, homogeneously mixing said solution with a water-insoluble cellulose or cellulose derivative and drying, and that the elution rate can be easily controlled by varying the contents of the potassium channel activator and crystalline cellulose, which resulted in the completion of the invention.

Accordingly, the present invention relates to, in producing a composition for solid medicine, comprising, as an active ingredient, a potassium channel activator and a pharmaceutically acceptable water-insoluble cellulose polymer, a method for producing a composition for solid medicine, which is characterized by dissolving a potassium channel activator in a solvent to give a medical solution, adding said medical solution to a water-insoluble cellulose polymer inert to said solvent in an amount necessary and sufficient to achieve a predetermined elution rate, homogeneously mixing them and drying the mixture to remove the solvent.

The composition for solid medicine thus obtained can be used as it is as a powder or can be used widely as a so-called solid preparation such as granules, tablets or capsules, which is formulated according to a known preparation technique.

The "potassium channel activator (potassium channel opener)" to be used for the method of the present invention may be any as long as it is a solid active compound exhibiting antihypertensive action or coronary vasodilating action upon activation of a potassium channel. For example, pyridine derivatives such as nicorandil and pinacidil and chromane derivatives represented by chromakalim of the following formulas are exemplified.

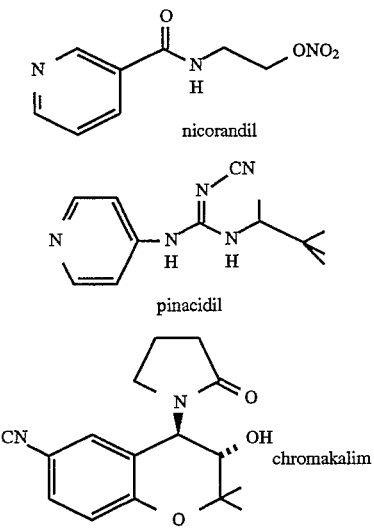

Examples of such compounds, particularly those of chromane derivatives, include the compounds described in Japanese Patent Unexamined Publication Nos. 176282/1984, 303977/1988, 170376/1988, 38087/1989, 151571/1989, 287083/1989, 316384/1989, 316385/1989, 180/1990, 223574/1990, 42074/1990, 49788/1990, 72171/1990, 104589/1990, 258781/1990, 279377/1991 and 502002/1992. The method of the present invention is particularly suitably applied to, but not limited to, chromakalim derivatives.

As used herein, the "solid preparation" includes all preparations wherein the active ingredient is a solid, and may have, without limitation, any preparation form classified under powder, granule, tablet, capsule, as well as suspension, emulsion and so on.

The "solvent" to be used in the present invention may be any as long as it dissolves a potassium channel activator as an active ingredient, and does not allow dissolution of water-insoluble cellulose polymers. In view of the steps to follow, volatile solvents superior in crystal precipitation performance and described in Japan Pharmacopoeia, such as ethanol, dichloromethane, isopropyl alcohol and acetone, are preferable.

These solvents may be used alone or in combination, or optionally in the form of a mixed solvent with water.

The "pharmaceutically acceptable water-insoluble cellulose polymer" to be used in the present invention is a water-insoluble cellulose or cellulose derivative conventionally employed in the field of formulation of preparations. Examples thereof include crystalline cellulose (MCC), carboxymethyl cellulose (CMC), calcium carboxymethyl cellulose (CMC-Ca), low substituted hydroxypropyl cellulose (L-HPC) and Carmellose sodium (crosslinked CMC-Na), with preference given to MCC, CMC and CMC-Ca.

The method for producing the composition for solid medicine of the present invention is explained in the following.

A potassium channel activator as an active ingredient is dissolved in a solvent such as ethanol, acetone and isopropyl alcohol to give a medical solution. This solution is added to a water-insoluble cellulose polymer, mixed and dried to give powdery granules comprising a potassium channel activator as an active ingredient and pharmaceutically acceptable water-insoluble cellulose polymer.

The proportion of the potassium channel activator and the solvent is not particularly determined, and the solvent is used in an amount sufficient to completely dissolve said activator. It should be noted that an extremely small amount of the solvent prevents homogeneous mixing thereof with a cellulose polymer in the next step, while too much amount of the solvent requires much time for drying etc. to result in lowering productivity. A solvent is generally preferably used in a 3 to 50-fold amount relative to a potassium channel activator. A solubilizer such as polyoxyl stearate 40, polysorbate 80, polyoxyethylene stearate and sodium lauryl sulfate may be used for dissolution of the activator in a solvent.

With regard to the addition of a cellulose polymer to a medicine, the experimental examples to be described later revealed that the initial elution rate could be lowered or controlled by reducing the amount of the cellulose polymer to be added. Accordingly, their proportions are appropriately determined according to the design of a desired medicine. For example, a preparation exhibiting an elution rate of 30% in 10 minutes is obtained by adding a cellulose polymer to a potassium channel activator in a weight ratio of 1:5 (potassium channel activator being 1), which is a necessary and sufficient amount to achieve the predetermined elution rate, as is evident from Example 1 to follow. While the preferable content ratio (weight ratio) is 1:5–15, this ratio is not limitative and may be altered according to the object.

Mixing can be done, for example, using a known stirrer-mixer such as high speed mixer and the like.

Drying can be done by any known method such as fluidized bed drying and ventilation drying.

While the thus-obtained granular or powdery preparation may be used as it is as a powder, it is preferably used upon formulation into granule, tablet, capsule or the like by a conventional method. Such tablet, granule, capsule and the like can be produced by a known method. For formulation of solid preparations such as tablet, known excipients such as lactose, crystalline cellulose, corn starch, magnesium aluminate metasilicate, hydrous silicon dioxide and hydroxypropyl starch, and binders such as polyvinyl pyrrolidone, hydroxypropyl cellulose, hydroxypropylmethyl cellulose and methyl cellulose can be used. In addition, lubricants such as magnesium stearate, talc and castor oil, disintegrants such as Carmellose sodium and carboxymethyl cellulose, coloring agents and the like may be added as appropriate.

BRIEF DESCRIPTION OF THE DRAWINGS

FIG. 1 explains the results of elution test conducted in Experimental Example 1; FIG. 2 explains the results of elution test conducted in Experimental Example 2; and FIG. 3 explains the results of elution test conducted in Experimental Example 3.

DETAILED DESCRIPTION OF PREFERRED EMBODIMENTS

The present invention is hereinafter explained by reference to Examples and Experimental Examples, to which the present invention is not limited.

Example 1

(+)-(3S,4R)-trans-4-(N-Acetyl-N-benzyloxy)amino-6-cyano-3,4-dihydro-2,2-dimethyl-2H-1-benzopyran-3-ol (Compound A, 20 g) was completely dissolved in ethanol (80 ml) at 70° C. This solution was entirely added to crystalline cellulose (100 g), and the mixture was stirred in a high speed mixer (manufactured by Fukae Kogyo) for 5 minutes and dried at 60° C. The composition (15 g) obtained by the above-mentioned steps, lactose (377.5 g), crystalline cellulose (25 g) and corn starch (110 g) were mixed. The mixture was granulated by a fluidized bed granulator (MP-01 manufactured by POWREX) using a 10% aqueous solution of polyvinyl pyrrolidone VA64 (300 g) as a binder, and dried. Carmellose sodium (40 g) and magnesium stearate (2.5 g) were added and mixed, after which the mixture was compressed by a conventional method to give tablets containing 0.5 mg of Compound A per tablet.

Example 2

In the same manner as in Example 1, tablets containing 0.5 mg of Compound A per tablet were produced using Compound A (15 g), crystalline cellulose (90 g) and ethanol (60 ml).

Three lots of tablets were produced in completely the same manner as above.

Example 3

In the same manner as in Example 1, tablets containing 0.5 mg of Compound A per tablet were produced using Compound A (15 g), crystalline cellulose (105 g) and ethanol (60 ml).

Example 4

In the same manner as in Example 1, tablets containing 0.5 mg of Compound A per tablet were produced using Compound A (10 g), crystalline cellulose (100 g) and ethanol (40 ml).

For comparison, various tablets were produced from bulks having varied particle size, by a conventional method without dissolving in a solvent.

Comparative Example 1

Compound A bulk (20 g, average particle size 210 μm) and crystalline cellulose (100 g) were mixed. Lactose (377.5 g), crystalline cellulose (25 g) and corn starch (110 g) were mixed with the obtained mixture (15 g). The mixture was granulated by a fluidized bed granulator (MP-01 manufactured by POWREX) using a 10% aqueous solution of polyvinyl pyrrolidone VA64 (300 g) as a binder, and dried. Carmellose sodium (40 g) and magnesium stearate (2.5 g) were added and mixed, after which the mixture was compressed by a conventional method to give tablets containing 0.5 mg of Compound A per tablet.

Comparative Example 2

In the same manner as in Comparative Example 1, tablets containing 0.5 mg of Compound A per tablet were produced using Compound A bulk (20 g, average particle size 350 μm) and crystalline cellulose (100 g).

Comparative Example 3

In the same manner as in Comparative Example 1, tablets containing 0.5 mg of Compound A per tablet were produced using Compound A bulk (20 g, average particle size 220 μm) and crystalline cellulose (100 g).

Comparative Example 4

In the same manner as in Comparative Example 1, tablets containing 0.5 mg of Compound A per tablet were produced using Compound A bulk (20 g, average particle size 310 μm) and crystalline cellulose (100 g).

Example 5

Compound A (15 g) was completely dissolved in ethanol (60 ml) at 70° C. This solution was added to carboxymethyl cellulose (90 g), and the mixture was stirred in a high speed mixer (manufactured by Fukae Kogyo) for 5 minutes and dried at 60° C. Using the composition obtained by the above-mentioned steps, tablets containing 0.5 mg of Compound A per tablet were produced in the same manner as in Example 1.

Example 6

Compound A (15 g) was completely dissolved in isopropyl alcohol (60 ml) at 70° C. This solution was added to crystalline cellulose (90 g), and the mixture was stirred in a high speed mixer (manufactured by Fukae Kogyo) for 5 minutes and dried at 60° C. Using the composition obtained by the above-mentioned steps, tablets containing 0.5 mg of Compound A per tablet were produced in the same manner as in Example 1.

The content ratio of the potassium channel activator and cellulose polymer used in the above-mentioned Examples and Comparative Examples is shown in Table 1. The mixing ratio of various additives for producing final preparations is respectively shown in Table 1 and Table 2.

TABLE 1

| | Composition (potassium channel activator + cellulose) | | | | | |
|---|---|---|---|---|---|---|
| | Activator (a) Compound A | | | Solvent | | |
| Ex. No. | (particle size, μm) | Cellulose (b) | | Ethanol | Isopropyl alcohol | a:b |
| | | MMC | CMC | | | |
| Ex. 1 | 20 g | 100 g | | 80 ml | | 1:5 |
| Ex. 2 | 15 g | 90 g | | 60 ml | | 1:6 |
| Ex. 3 | 15 g | 105 g | | 60 ml | | 1:7 |
| Ex. 4 | 10 g | 100 g | | 40 ml | | 1:10 |
| Comp. Ex. 1 | 20 g (210) | 100 g | | | | 1:5 |
| Comp. Ex. 2 | 20 g (350) | 100 g | | | | 1:5 |
| Comp. | 20 g | 100 g | | | | 1:5 |

TABLE 1-continued

| | Composition (potassium channel activator + cellulose) | | | | | |
|---|---|---|---|---|---|---|
| | Activator (a) Compound A | | | Solvent | | |
| Ex. No. | (particle size, μm) | Cellulose (b) | | Ethanol | Isopropyl alcohol | a:b |
| | | MMC | CMC | | | |
| Ex. 3 | (220) | | | | | |
| Comp. Ex. 4 | 20 g (310) | 100 g | | | | 1:5 |
| Ex. 5 | 15 g | | 90 g | 60 ml | | 1:6 |
| Ex. 6 | 15 g | 90 g | | | 60 ml | 1:6 |

TABLE 2

| | Formulation for final preparation, unit:g | | | | | | | |
|---|---|---|---|---|---|---|---|---|
| Ex. No. | Composition | Lactose | Corn starch | Crystalline cellulose | Polyvinyl pyrrolidone VA64 | Carmellose sodium | Magnesium stearate | Total | Activator per tablet (mg) |
| Ex. 1 | 15 | 377.5 | 110 | 25 | 30 | 40 | 2.5 | 600 | 0.5 |
| Ex. 2 | 17.5 | 377.5 | 110 | 22.5 | 30 | 40 | 2.5 | 600 | 0.5 |
| Ex. 3 | 20 | 377.5 | 110 | 20 | 30 | 40 | 2.5 | 600 | 0.5 |
| Ex. 4 | 27.5 | 377.5 | 110 | 12.5 | 30 | 40 | 2.5 | 600 | 0.5 |
| Comp. Ex. 1 | 15 | 377.5 | 110 | 25 | 30 | 40 | 2.5 | 600 | 0.5 |
| Comp. Ex. 2 | 15 | 377.5 | 110 | 25 | 30 | 40 | 2.5 | 600 | 0.5 |
| Comp. Ex. 3 | 15 | 377.5 | 110 | 25 | 30 | 40 | 2.5 | 600 | 0.5 |
| Comp. Ex. 4 | 15 | 377.5 | 110 | 25 | 30 | 40 | 2.5 | 600 | 0.5 |
| Ex. 5 | 15 | 377.5 | 110 | 25 | 30 | 40 | 2.5 | 600 | 0.5 |
| Ex. 6 | 15 | 377.5 | 110 | 25 | 30 | 40 | 2.5 | 600 | 0.5 |

The Experimental Examples regarding the elution rate are given in the following.

Experimental Example 1

Using the tablets obtained in Examples 1–4 as test samples, dissolution tests were conducted. One test sample tablet was added to 900 ml of purified water and subjected to the test according to the paddle method described in Japan Pharmacopoeia, XII (rotation speed 100 rpm). Aliquots of the test solution were taken periodically, and the amount of Compound A eluted was quantitatively determined by high performance liquid chromatography (HPLC). The analysis conditions were as follows. The results are shown in FIG. 1.
HPLC quantitative assay:
  Equipment:Shimadzu LC-10A
  Column:YMC-Pack ODS-A, 150×6.0 mm
  Mobile phase:70% acetonitrile
  Flow rate:1.0 ml/min
  Detection wavelength:254 nm The results of the above tests revealed that adjusting the content ratio of the potassium channel activator and the cellulose polymer enabled suppression of elution rate, particularly initial elution rate. The suppression of elution rate is indicative of the cause being decreased surface area involved in dissolution, due to the formation of a kind of complex of Compound A and crystalline cellulose to include Compound A crystals with crystalline cellulose or coagulation of the crystals.

Experimental Example 2

Using the three lots of tablets produced by the method of Example 2 and the tablets produced in Comparative Examples 1–4 as test samples, elution tests were conducted. The test conditions were the same as in Experimental Example 1. The results are shown in FIG. 2.

According to the test results as described above, the elution patterns of the tablets of Comparative Examples 1–4, which differed only in bulk particle distribution and were same in other conditions, were quite different from each other. In contrast, all three lots of tablets of Example 2 produced according to the present invention showed completely the same elution pattern. Therefrom it is evident that the present invention eliminates the variance in elution rate found in manufactured lots.

Experimental Example 3

Using the tablets of Example 2, the tablets of Example 5 using CMC as a cellulose and tablets produced in Example 6 using IPA as a solvent as test samples, elution tests were conducted. The test conditions were the same as in Experimental Example 1.

The results are shown in FIG. 3.

The test results clearly showed that the present invention achieved a constant elution pattern, irrespective of the kind of cellulose polymers and solvents.

Industrial Applicability

As is evident from the foregoing description and test results, a solid preparation with suppressed initial elution rate can be produced with good reproducibility by an extremely simple technique according to the present invention, which comprises dissolving a potassium channel activator in a solvent, homogeneously mixing same with a crystalline cellulose and the like and drying same. In addition, elution rate can be controlled with ease by merely changing the content ratio of potassium channel activator and cellulose polymer.

What is claimed is:

1. A method for producing a solid pharmaceutical composition, comprising the steps of:

dissolving a pharmaceutically acceptable potassium channel activator in a solvent to form a solution, combining the solution with a pharmaceutically acceptable water-insoluble cellulose polymer which is inert to the solvent in an amount sufficient to achieve a predetermined elution rate, wherein the solvent does not dissolve the water-insoluble cellulose polymer, homogeneously mixing the polymer in the solution to form a mixture, and drying the mixture to remove the solvent, thereby to obtain the solid pharmaceutical composition.

2. The method according to claim 1, wherein the pharmaceutically acceptable potassium channel activator is a chromane derivative.

3. The method according to claim 1, wherein the pharmaceutically acceptable water-insoluble cellulose polymer is crystalline cellulose, carboxylmethyl cellulose, carboxymethyl cellulose-calcium or a mixture thereof.

4. The method according to claim 2, wherein the pharmaceutically acceptable water-insoluble cellulose polymer is crystalline cellulose, carboxylmethyl cellulose, carboxymethyl cellulose-calcium or a mixture thereof.

5. The method according to claim 1, wherein the solvent is ethanol, dichloromethane, isopropyl alcohol or acetone.

6. A solid pharmaceutical composition which is obtained by the method according to claim 1.

7. A solid pharmaceutical composition which is obtained by the method according to claim 2.

8. A solid pharmaceutical composition which is obtained by the method according to claim 3.

9. A solid pharmaceutical composition which is obtained by the method according to claim 4.

10. A solid pharmaceutical composition which is obtained by the method according to claim 5.

* * * * *